(12) United States Patent
Sunwoo et al.

(10) Patent No.: US 6,998,135 B1
(45) Date of Patent: Feb. 14, 2006

(54) DEMINERALIZED CORTICOCANCELLOUS BONE SHEET

(75) Inventors: Moon Hae Sunwoo, Old Tappan, NJ (US); Arthur A. Gertzman, Stony Point, NY (US); Bruce W. Stroever, Long Valley, NJ (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 465 days.

(21) Appl. No.: 09/853,761

(22) Filed: May 14, 2001

Related U.S. Application Data

(63) Continuation-in-part of application No. 09/413,815, filed on Oct. 7, 1999, now Pat. No. 6,326,018, which is a continuation of application No. 09/031,750, filed on Feb. 27, 1998, now Pat. No. 6,030,635.

(51) Int. Cl.
*A61F 13/00* (2006.01)
*A61F 2/00* (2006.01)

(52) U.S. Cl. ........................ 424/422; 424/423
(58) Field of Classification Search ................ 424/423, 424/422, 400
See application file for complete search history.

(56) References Cited

U.S. PATENT DOCUMENTS

| | | | |
|---|---|---|---|
| 2,621,145 A | 12/1952 | Sand | |
| 4,394,370 A | 7/1983 | Jefferies | |
| 4,430,760 A | 2/1984 | Smestad | |
| 4,472,840 A | 9/1984 | Jefferies | |
| 4,485,096 A | 11/1984 | Bell | |
| 4,485,097 A | 11/1984 | Bell | |
| 4,678,470 A | 7/1987 | Nashef et al. | |
| 4,950,296 A | 8/1990 | McIntyre | |
| 5,053,049 A | 10/1991 | Cambell | |
| 5,306,304 A | 4/1994 | Gendler | |
| 5,464,439 A | 11/1995 | Gendler | |
| 5,507,813 A | 4/1996 | Dowd et al. | |
| 5,556,430 A | 9/1996 | Gendler | |
| 5,899,939 A * | 5/1999 | Boyce et al. | 623/16 |
| 6,189,537 B1 | 2/2001 | Wolfinbarger, Jr. | |
| 6,294,187 B1 * | 9/2001 | Boyce et al. | 424/422 |
| 6,305,379 B1 | 10/2001 | Wolfinbarger, Jr. | |

* cited by examiner

*Primary Examiner*—Thurman K. Page
*Assistant Examiner*—Humera N. Sheikh
(74) *Attorney, Agent, or Firm*—John S. Hale; Gipple & Hale

(57) ABSTRACT

A flexible, demineralized unitary bone sheet comprised of cortical cancellous bone having a residual calcium weight of 3.0% to 8.0% with a hyaluronic acid component having a molecular weight of 700,000 to 1,500,000 with the weight of the same ranging from 1% to about 5% of the total sheet weight. The bone sheet is adapted for use during the in vivo repair of a mammalian or animal skeletal system with the thickness of the cortical cancellous sheet ranging from 2.0 mm to about 8.0 mm. The bone sheet has sufficient flexibility to allow the sheet to be shaped to conform to the configuration of a skeletal region to be repaired and sufficient tensile strength to allow the sheet to be so shaped without damage to the sheet.

36 Claims, 2 Drawing Sheets

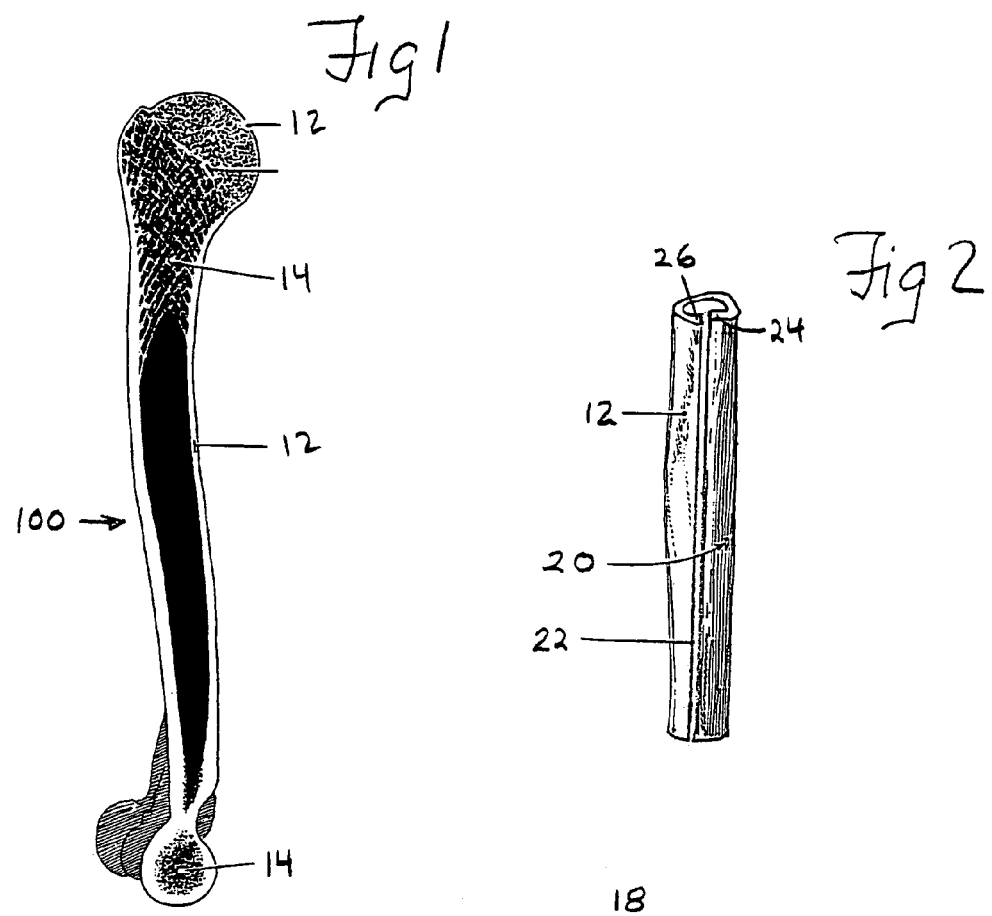
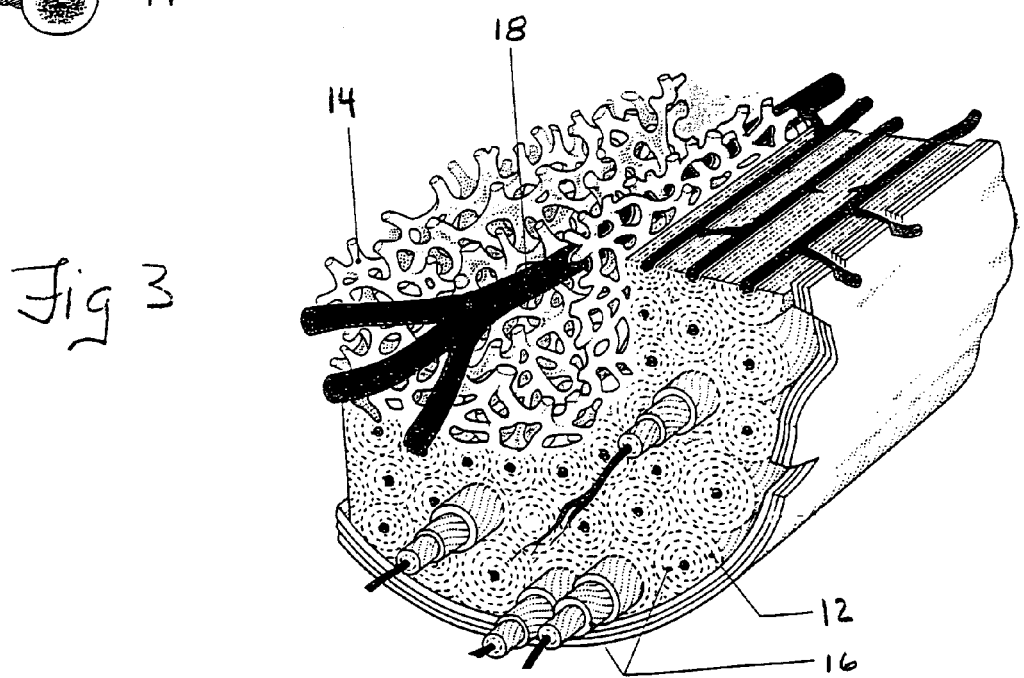

DEMINERALIZED CORTICOCANCELLOUS BONE SHEET

RELATED APPLICATIONS

This is a continuation-in-part of U.S. patent application Ser. No. 09/413,815 filed Oct. 7, 1999, now U.S. Pat. No. 6,326,018 which is a continuation of U.S. patent application Ser. No. 09/031,750, filed Feb. 27, 1998 which has issued into U.S. Pat. No. 6,030,635.

FIELD OF THE INVENTION

The present invention relates to a bone implant for use in the repair and replacement of the various portions of the human skeletal system. More particularly, it is directed toward a unitary sheet of demineralized cortical cancellous bone for use in the repair and replacement of various portions of the human skeletal system.

BACKGROUND OF THE INVENTION

The repair, as well as the replacement, of diseased and damaged human bone have been the subject of substantial research efforts over the past several decades. This research has yielded advances in the reconstruction of many areas of the human skeletal system. As a result of these advances, bone replacements and repair are presently being undertaken in several areas including the restructuring of the craniofacial system, bone repair, the introduction of artificial knee and hip joints, and the application of additional features during cosmetic surgery.

The biological mechanisms underlying the reconstruction and repair varies according to the type of bone implant selected. New bone can be formed by three basic mechanisms: osteogenesis, osteoconduction and osteoinduction. In osteogenic transplantation, viable osteoblasts and osteoclasts are moved from one body location to another where they establish centers of bone formation. Allologous tissue, cancellous bone and marrow grafts provide such viable cells. As a generalization, spongy cancellous bone permits rapid and usually complete revascularization.

In the transplantation of large segments of cortical bone or allogenic banked bone, direct osteogenesis does not occur. In these cases, osteoconduction transpires—the dead bone acts as a scaffold for the ingrowth of blood vessels, followed by the resorption of the implant and deposition of new bone. This process is slow, sometimes requiring years to reunite a large segmental defect. As a generalization, cortical bone has high strength and undergoes osteoclastic digestion of the bone and revascularizes through pre-existing anatomical channels, a relatively slow process.

Osteoinduction is the phenotypic conversion of connective tissue into bone by an appropriate stimulus. As this concept implies, formation of bone can be induced at even non-skeletal sites. Osteoinduction is the preferred method of providing new bone growth as allografts of this type are typically incorporated into the host bone within several weeks. In contrast, osteoconductive grafts have been found to be non-incorporated as long as one year after implantation.

In order to provide an environment suitable for osteoinduction, a material should be selected which is not only capable of inducing osteogenesis throughout its volume, but is also biocompatible, non-inflammatory, and possesses the ability to be ultimately resorbed by the body and replaced with new, natural bone.

During surgery, the allograft implants are manipulated to fit a given site and may be required to be folded or wrapped around a boney defect to provide the osteoconductive material thereto.

There thus exists a need for a flexible bone sheet with high tear strength which is easy to use and promotes rapid bone growth.

Initial attempts to manufacture and obtain bone sheets are shown in U.S. Pat. No. 2,621,145 in which particles of bone 1–2 mm in size were placed on a sterile carrier strip of material. The bone particles were sprayed or dripped with a citrated or heparinized plasma on the flexible carrier strip, made of a plastic material such as cellophane, to form a bone mat.

One approach to sheet type bone repair and reconstruction is disclosed in U.S. Pat. Nos. 4,472,840 and 4,394,370, the later being a divisional of the '840 patent. These patents are directed toward bone graft material, using a complex of reconstituted collagen and demineralized bone particles. This material may be fabricated into a number of forms, such as a thin membrane. One advantage of this material, as stated in the reference, is in its ability to promote bone regeneration and the use of bone particles in implant materials has been shown to induce greater quantities of new bone growth than unmodified, larger particles such as blocks or chips. Moreover, large, unmodified sections of demineralized bone are noted in the reference to induce osteogenesis only at their surface, not within the graft itself.

U.S. Pat. Nos. 4,485,096 and 4,485,097 disclose the use of bone particulates, or powders incorporated into hydrated collagen lattices contracted with fibroblast cells. The material may, if desired, be cast into sheets. One method requires the material to be coated onto a mesh of polytetrafluoroethylene (PTFE) or stainless steel which serves to maintain the length and width of the material. The inclusion of such a dimensional stabilizing material is required due to the presence of fibroblast cells because if left unrestrained, the collagen lattice would undergo contractions in all dimensions.

A related type of bone material is found in U.S. Pat. No. 4,430,760 which discloses a bone prosthesis comprising demineralized bone or dentin powder contained in a porous, medical grade casing manufactured from biocompatible polymeric fibers or a micro porous membrane. Demineralized bone powder is used as a particulate as it is more readily invaded by osteogenic cells than solid, one-piece demineralized bone. Another bone sheet is disclosed in U.S. Pat. No. 5,507,813 which utilizes elongate demineralized bone particles obtained by milling or shredding bone. The sheet is formed by a wet layering process in which slurry is applied to a porous support and the same is drained and dried to form a composite sheet with a median thickness of from about 0.002 mm to about 1.0 mm.

Yet another material is described in U.S. Pat. No. 4,678,470 which provides a bone grafting material which is produced from allogenic or xenogenic bone which may be pulverized, used as a large block, or machined into a precise predetermined shape depending on the bone defect being repaired. The method for deriving the material comprises tanning the bone with glutaraldehyde. This treatment of the material by tanning is noted as stabilizing the material as well as cross-linking the proteins. The bone may also be demineralized. The resulting demineralized bone is noted to have a "spongier" texture and thus finds use only in non-weight bearing situations, i.e., repair of small defects, filling of small tunnels or other hollow areas, cosmetic surgery, and similar uses.

A shaped bone piece which is cut to the desired usage shape is described in U.S. Pat. No. 5,053,049. The shaped piece is demineralized and tanned with a tanning reagent.

A bone sheet which is cut from organic bone matrix is disclosed in U.S. Pat. No. 5,306,304. In this reference, natural bone after having been cleaned of blood and lipid residue, is cut with a diamond wafering blade into a sheet having a thickness ranging from 0.05 to about 1.5 millimeters. The bone sheet is then demineralized until the sheet is flexible (bent or deformed from original configuration) for primary use in dental related implants.

U.S. Pat. Nos. 5,464,439 and 5,556,430 to the same inventor as the '304 patent are also directed toward the cutting of a thin sheet of bone from natural bone, the sheet having a thickness ranging from about 0.05 mm to about 1.5 mm and then demineralizing the same.

Another U.S. Pat. No. 5,899,939 is directed toward the construction of a multiple layer sheet of bone with fully mineralized or partially demineralized cortical bone. In addition to cortical bone, other materials such as hydroxyapatite can be used for the layer composition. The cortical portion of bone is taken from the diaphyseal region and cut into various thickness using a diamond bladed saw. The cortical bone layers of varying width are monolithic sections or multi-component sections and the layers, both bone and other materials, are adhesively secured together.

U.S. Pat. No. 4,950,296 shows the use of a cortical dowel having a cavity into which a cancerous plug is inserted to aid in bone formation.

Other processes used in the field of periodontics also utilize an expanded polytetrafluoroethylene material, e.g., GORETEX® e-PTFE, which is stated to be flexible and biocompatible.

Thus, and despite the processes and materials known in the art, there exists a need for a bone sheet material that possesses all of the aforementioned advantageous properties, e.g., biocompatible, non-inflammatory, capable of inducing osteogenesis, the ability to be ultimately resorbed by the body and replaced with natural bone, while not sacrificing flexibility, strength or dimensional stability thereof.

SUMMARY OF THE INVENTION

It has now been discovered that bone matrix taken from the cortical cancerous bone interface can be sliced into sheets ranging in thickness from 2.0 mm to 8.0 mm, partially or less than completely demineralized and treated with hyaluronic acid so that the sheets have unexpected properties. The bone sheets thus cut and demineralized are flexible while exhibiting significant tensile strength which is useful for the in vivo repair, replacement or reformation of preselected portions of a skeletal system. The bone sheet comprises a continuous unitary sheet of demineralized natural bone, having a thickness such that the sheet has sufficient flexibility to allow the sheet to be shaped to conform to the configuration of a skeletal region to be repaired and sufficient tensile strength to allow the sheet to be so shaped without damage to the sheet.

An additional method is drawn toward the sheet manufacture which comprises cleaning and demineralization of a tubular shaped bone and cutting the bone along a longitudinal axis. Both of the now separated ends of the tube are then pulled away from each other to present a substantially flat bone sheet which is then held in a form press for a period of time.

It is an object of the invention to provide a demineralized bone sheet with a residual calcium weight ranging from 0.25% to 8.0% for optimum bone formation at the application site.

It is also an object of the invention to create a bone sheet material for repairing defects which can be easily handled by the physician and does not destabilize when contacting blood flow or irrigation at the surgical site.

It is another object of the invention to utilize a continuous unitary sheet of cortical cancellous demineralized bone taken from a single bone.

It is an additional object of the invention to coat or impregnate a high molecular weight non-toxic hyaluronic acid solution with a sodium phosphate buffer in the bone sheet to present the sheet in a state of physiological osmolality (isotonic) at the wound site and provide a flexible sheet of bone material.

It is another object of the invention to create a demineralized bone sheet which does not interfere with healing at the wound site.

It is an additional object of the invention to create a composite cortical cancellous bone sheet with a physiological pH of 7.4.

It is yet another object of the invention to use a high molecular weight sodium hylauronic with a buffered, isotonic demineralized bone sheet to aid in healing at the bone defect site.

These and other objects, advantages, and novel features of the present invention will become apparent when considered with the teachings contained in the detailed disclosure which along with the accompanying drawings constitute a part of this specification and illustrate embodiments of the invention which together with the description serve to explain the principles of the invention.

BRIEF DESCRIPTION OF THE DRAWINGS

FIG. 1 is a perspective view of a bone used to make the present bone sheet invention;

FIG. 2 is a cut tubular section of the bone partially in cross section taken from the bone of FIG. 1;

FIG. 3 is an enlarged cross sectional portion of the bone of FIG. 1 showing the relationship between the cortical and cancerous layers;

DETAILED DESCRIPTION OF THE INVENTION

Figure 4:
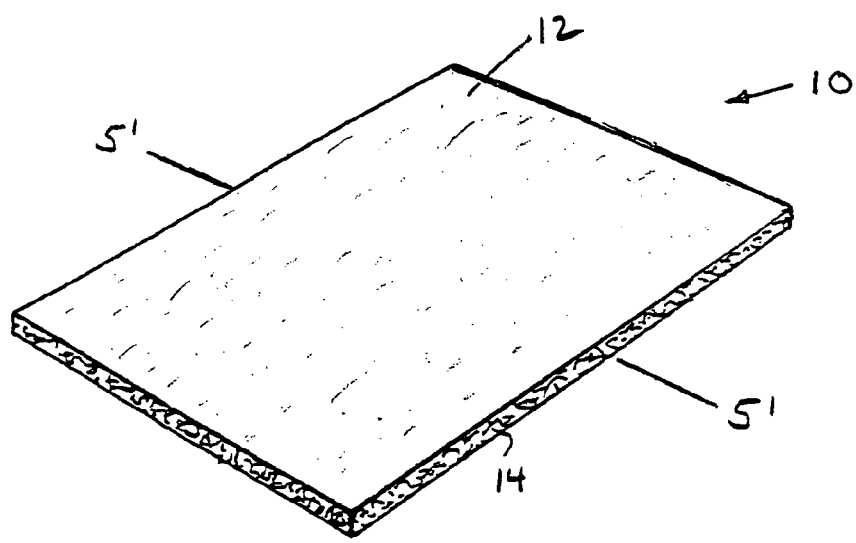
FIG. 4 is a perspective view of a bone sheet of the present invention.
Figure 5:
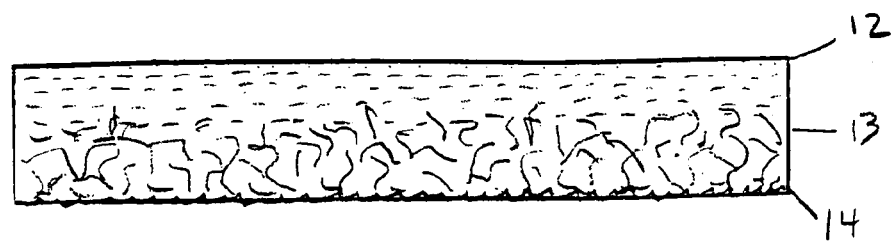
FIG. 5 is an enlarged cross sectional view of a bone sheet of the invention taken across line 5'—5' of FIG. 4 showing the cortical and cancellous layers.

While the present invention and best mode of the invention is shown in FIGS. 4 and 5 and will be described in connection with certain preferred embodiments, it is not intended that the present invention be so limited. On the contrary, it is intended to cover all alternatives, modifications, and equivalent arrangements as may be included within the spirit and scope of the invention as defined by the appended claims.

The present invention provides a novel sheet material for the repair and replacement of a portion of a skeletal system, e.g., the human skeletal system and method for making the sheet material. FIGS. 1 and 3 show a bone 100 having a cortical bone portion 12, a cancellous bone portion 14, Haversian canals 16 and a nutrient artery 18. The material comprises a continuous unitary sheet 10 of demineralized natural bone having a predetermined thickness. While such material has previously been cut from cortical bone it has been found that a sheet cut from bone including the cortical, the cortical/cancellous interface and cancerous portions results in a bone sheet 10 which when demineralized has many useful properties. Generally cortical bone 12 is between 5% to 30% porous while cancerous bone 14 ranges from between 35% to 90% porous. The cortical layer 12 has a cortical cancerous interface 13 with the cancerous bone layer which contains both cortical and cancerous bone structure. The bone sheet 10 while somewhat thick is flexible while retaining its structural and dimensional integrity both prior to and after hydration and additionally possessing significant tensile strength. The cancellous section 14 of the bone sheet 10 is able to hold buffered hyaluronic acid and bone morphogenic proteins to provide maximum bone grown when implanted onto the graft site.

Although demineralized bone heretofore has existed in the art, no one has previously produced demineralized bone in the form of thin sheets ranging from about 2.0 mm to about 8.0 mm in thickness incorporating cortical bone, the interface area between the cortical and cancerous bone and cancerous bone so that both cortical and cancerous bone appear in the same sheet. Indeed, it is quite surprising and unexpected that a thin sheet of this dual composition cortical and cancellous demineralized bone could be produced having both significant flexibility and tensile strength. Nothing in the art heretofore indicated that such a thin sheet of demineralized bone could be made of both types of bone and maintain desirable flexibility and tensile strength. Consequently the cortical layer 12 of the bone preferably ranges in thickness from about 1 mm to about 3 mm up to 5 mm and the cancerous layer 14 of the bone preferably ranges in thickness from about 1 mm to about 3 mm up to 5 mm in thickness. However, the thickness for either layer can be extended another 2 mm.

The bone itself may be produced from any natural bone as shown in FIG. 1. Generally, the bone material is harvested from any suitable vertebrate but the preferred usage is bone material harvested from humans. The harvested bone material may be further processed by various cleaning techniques well known in the art to remove substantially all marrow, fat, blood and lipid residue. The resulting bone sheet may be cut into plates of approximately 2.0–8.0 mm in thickness with a width and length from 1 to 20 centimeters using a Fleetwood model SO 200AL bandsaw. Cutting of the bone should be undertaken with continuous irrigation of the blade to prevent over heating of the bone. Bone sheets can be taken from the proximal tibua plateau, the iliac lateral wall, metatarsal or other flat zones of bones with adjacent cancellous sections. Alternatively, a generally tubular shaped bone piece 20 as shown in FIG. 2 is cleaned to remove bone marrow, fat, blood and lipids and is then cut 22 along the longitudinal axis. After demineralization, the separated ends 24 and 26 of the bone piece 20 are pulled apart to form a substantially flat bone sheet 10. If desired, the cortical surface of the sheet 10 could be longitudinally scored to ease the formation into a flat sheet. The resulting bone is further processed to remove any remaining blood and lipids and then demineralized until it contains from 0.25% to 8.0% by residual calcium. Demineralization of the bone is subsequently conducted by any known method, e.g., subjecting the bone to different acids, clearing agents, electrolysis or any combination of the foregoing. In the present invention, the demineralization treatment was done with 0.6N hydrochloric acid at ambient temperature. It has been discovered that the aforementioned demineralized unitary bone matrix, of cortical and cancellous composition is flexible and induces osteogenesis throughout its thickness and ultimately is substantially completely resorbed by the living system into which it is implanted.

Preferably the demineralization process leaves the bone sheet with 3.0% to 8.0% residual calcium and significant flexibility. After demineralization hyaluronic acid or sodium hyaluronate (HA) or deviations thereof, a viscous and biocompatible high molecular weight hydrogel having a molecular weight of 700,000 Daltons to 3,000,000 Daltons at a concentration of 1.0 to 4.0 mg/ml is added to the demineralized cortical cancellous bone sheet to minimize bacterial contamination and to aid in bone formation. Preferably, the final processed bone sheet comprises from 95% to 99% bone weight and from 5% to 1% HA weight. The biocompatibility of HA is well established and its use in surgery is well known. The HA is mixed with a phosphate buffered saline having a pH to counter the acidic nature of the HA to arrive at a bone sheet osmolality of about 290 mmol/kg to 310 mmol/kg, preferably 300 mmol/kg and a pH of about 7.4±2. This neutral osmolality allows formation of new bone which starts without having the graft site regain neutrality over a period of time which can be from one week to four weeks. Thus, the demineralized sheet of cortical cancellous bone is pH balanced, non-hemolytic and non toxic.

The following are examples of human allograft bone sheet tissue according to the present invention:

EXAMPLE 1

Cortical strips are prepared from human tibial allograft tissue taken from a qualified donor.

The tibia bone is debrided and cleaned using an osteotome, elevator, and a wire wheel mounted on an MTF designed debridement machine. The proximal posterior epiphysis of the tibia is cut into unicortical strips of about 2.5 cm×2.5 cm using a Fleetwood model SO 200AL bandsaw. 2.5 cm×10 cm strips were taken from the diaphysis in the same manner.

The cancellous is trimmed to a uniform thickness using the Fleetwood model SO 200AL bandsaw with the average thickness of the strips being about 2 mm–8 mm. The strips are rinsed with a minimum of 1000 ml WFI (water for injection) to remove blood and lipids. The strips then are subjected to a succession of soaks and rinses as follows:

1. The strips are soaked in two liters of Tween 80 for thirty minutes in a Branson model # 2510 sonicator without heat.

2. After soaking, the strips are rinsed with a minimum of 1000 ml WFI.

3. After rinsing, the strips are soaked in 0.5 liter of peroxide in a graduated one liter beaker for 15 minutes.

4. After soaking, the strips are rinsed with a minimum of 1000 ml WFI.

5. After rinsing, the strips are soaked in 0.5 liter of 70% ethanol in a graduated one liter beaker for 60 minutes.

The tissue is then either triple bagged in Kapak and stored at −70c until further processing or is fully or partially demineralized to achieve the desired flexibility. The following demineralization process is used:

1. Each bone plate is soaked in 0.6N hydrochloric acid for sufficient time at room temperature to achieve a residual calcium concentration of 2%–8% (typically 60–180 minutes).

2. The bone plate is washed free of excess acid with pure water and then further washed with a 0.1M phosphate buffered saline until the wash discard is at a pH of about 7.2.

3. The wet bone plate is then immersed in a 1.8% (w/w) solution of pH 7.2 buffered sodium hyaluronate (HA) (molecular weight of 700,000 Daltons) solution. Excess HA was wiped off the bone plate.

4. The bone plate is then packaged in a sealed foil pouch to prevent further drying.

EXAMPLE 2

Cortical strips are prepared from human femoral allograft tissue taken from a qualified donor.

The femur bone is debrided and cleaned using an osteotome, elevator, and a wire wheel mounted on an MTF designed debridement machine. The distal anterior and posterior epjphysis of the femur is cut into unicortical strips of about 2.5 cm×2.5 cm using a Fleetwood model SO 200AL bandsaw.

The cancellous is trimmed to a uniform thickness using the Fleetwood model SO 200AL bandsaw with the average thickness of the strips being about 2 mm–8 mm.

The strips are rinsed with a minimum of 1000 ml WFI to remove blood and lipids. The strips are then subjected to a succession of soaks and rinses as follows:

1. The strips are soaked in two liters of Tween 80 for thirty minutes in a Branson model # 2510 sonicator without heat.

2. After soaking, the strips are rinsed with a minimum of 1000 ml WFI.

3. After rinsing, the strips are soaked in 0.5 liter of peroxide in a graduated one liter beaker for 15 minutes.

4. After soaking, the strips are rinsed with a minimum of 1000 ml WFI.

5. After rinsing, the strips are soaked in 0.5 liter of 70% ethanol in a graduated one liter beaker for 60 minutes.

The tissue is then triple bagged in Kapak and will be stored at −70c until further processing or is fully or partially demineralized to achieve the desired flexibility. The following demineralization process is used:

1. Each bone plate is soaked in 0.6N hydrochloric acid for sufficient time at room temperature to achieve a residual calcium concentration of 2%–8% (typically 60–180 minutes).

2. The bone plate is washed free of excess acid with pure water and then further washed with a 0.1M phosphate buffered saline until the wash discard is at a pH of about 7.2.

3. The wet bone plate is then immersed in a 1.8% (w/w) solution of pH 7.2 buffered sodium hyaluronate (HA) (molecular weight of 700,000 Daltons) solution. Excess HA was wiped off of the bone plate.

4. The bone plate is then packaged in a sealed foil pouch to prevent further drying.

EXAMPLE 3

Cortical strips are prepared from human pelvic allograft tissue taken from a qualified donor.

A Hemi-Pelvis bone is debrided and cleaned using an osteotome, elevator, and a wire wheel mounted on an MTF designed debridement machine. The pelvis is cut transversely into bi-cortical strips of about 1.5 cm×5.0 cm using a Fleetwood model SO 200AL bandsaw.

The strips are then be halved to produce unicortical/cancellous strips. The cancellous is trimmed to a uniform thickness using the Fleetwood model SO 200AL bandsaw with the average thickness of the strips being about 2 mm–5 mm.

The strips are rinsed with a minimum of 1000 ml WFI to remove blood and lipids. The strips are then subjected to a succession of soaks and rinses as follows:

1. The strips are soaked in two liters of Tween 80 for thirty minutes in a Branson model # 2510 sonicator without heat.

2. After soaking, the strips are rinsed with a minimum of 1000 ml WFI.

3. After rinsing, the strips are soaked in 0.5 liter of peroxide in a graduated one liter beaker for 15 minutes.

4. After soaking, the strips are rinsed with a minimum of 1000 ml WFI.

5. After rinsing, the strips are soaked in 0.5 liter of 70% ethanol in a graduated one liter beaker for 60 minutes.

The tissue is then triple bagged in Kapak and will be stored at −70c until further processing or is fully or partially demineralized to achieve the desired flexibility. The following demineralization process is used:

1. Each bone plate is soaked in 0.6N hydrochloric acid for sufficient time at room temperature to achieve a residual calcium concentration of 2%–8% (typically 60–180 minutes).

2. The bone plate is washed free of excess acid with pure water and then further washed with a 0.1M phosphate buffered saline until the wash discard is at a pH of about 7.2.

3. The wet bone plate is then immersed in a 1.8% (w/w) solution of pH 7.2 buffered sodium hyaluronate (HA) (molecular weight of 700,000 Daltons) solution. Excess HA was wiped off of the bone plate.

4. The bone plate is then packaged in a sealed foil pouch to prevent further drying.

EXAMPLE 4

Cortical strips are be prepared from human calcaneal allograft tissue taken from a qualified donor.

A calcaneus is debrided and cleaned using an osteotome, elevator, and a wire wheel mounted on an MTF designed debridement machine. The calcaneus is bisected longitudinally and cut into unicortical strips of about 1.5 cm×1.5 cm using a Fleetwood model SO 200AL bandsaw.

The cancellous is trimmed to a uniforn1 thickness using the Fleetwood model SO 200AL bandsaw with the average thickness of the strips being about 2 mm–8 mm.

The strips are rinsed with a minimum of 1000 ml WFI to remove blood and lipids. The strips are then subjected to a succession of soaks and rinses as follows:

1. The strips are soaked in two liters of Tween 80 for thirty minutes in a Branson model # 2510 sonicator without heat.

2. After soaking, the strips are rinsed with a minimum of 1000 ml WFI.

3. After rinsing, the strips are soaked in 0.5 liter of peroxide in a graduated one liter beaker for 15 minutes.

4. After soaking, the strips are rinsed with a minimum of 1000 ml WFI.

5. After rinsing, the strips are soaked in 0.5 liter of 700/G ethanol in a graduated one liter beaker for 60 minutes.

The tissue is then triple bagged in Kapak and will be stored at −70c until further processing or is fully or partially demineralized to achieve the desired flexibility. The following demineralization process can be used:

1. Each bone plate is soaked in 0.6N hydrochloric acid for sufficient time at room temperature to achieve a residual calcium concentration of 2%–8% (typically 60–180 minutes).

2. The bone plate is washed free of excess acid with pure water and then further washed with a 0.1M phosphate buffered saline until the wash discard is at a pH of about 7.2.

3. The wet bone plate is then immersed in a 1.8% (w/w) solution of pH 7.2 buffered sodium hyaluronate (HA) (molecular weight of 700,000 Daltons) solution. Excess HA was wiped off the bone plate.

4. The bone plate is then packaged in a sealed foil pouch to prevent further drying.

Using the aforesaid procedures, natural bone sheets having a length and width of about 1 to 20 centimeters and greater may be produced, this being limited only by the dimensions of the bone material supplied. The material may then be reduced to the desired length and width dimensions by cutting. Use of the term "sheet" throughout this disclosure is intended to encompass those portions of an original sheet which have been reduced to a desired length and width.

Additional examples of uses for the present material include the replacement, augmentation and recontouring of natural bone structures in orthopedic plastic and reconstructive surgery, cosmetic, otolaryngological and neurological surgical procedures. In view of the material's ability to be reabsorbed into the living system after promoting osteogenesis, a subsequent surgical procedure to remove any remaining portion of the material is eliminated.

Other advantages include the flexibility of the material. The material is flexible at the time it is manufactured as well as after hydration. By use of the term "flexible," it is contemplated that the material may be deformed or bent from an original configuration. Flexibility is a desirable property because it is often desirable to be able to bend and shape the material such that, after the area is completely healed, the contour of the bone being repaired matches the contour of the original bone, or matches the original bone as closely as possible. The cortical cancerous material also advantageously provides a tensile strength which is higher than other materials currently used which are capable of osteoinductive activity throughout the volume of the material. Generally, the method for using the present natural bone sheet comprises affixing the material onto the portion of the skeletal system in need of repair or replacement. Affixation may be accomplished by any known surgical technique.

Although the present material and methods are useful as for treatment of humans, it is also useful in treating many different types of animals, such as dogs, horses and the like.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive. Variations and changes may be made by others without departing from the scope of the present inventions defined by the following claims.

What we claim is:

1. A sterile flexible bone sheet for use during the in vivo replacement or reformation of preselected portions of an animal skeletal system comprising a continuous integral unitary sheet of demineralized natural bone with a cortical layer and a cancellous layer, said cortical layer interfacing with said cancellous layer through a cortical cancellous section, the thickness of said sheet ranging from 2.0 mm to 8.0 mm, the sheet being capable of being bent from its original shape to conform to the configuration of a skeletal region to be repaired without damage to the sheet, said sheet being capable of inducing osteogenesis at the skeletal region.

2. A sterile flexible bone sheet according to claim 1 wherein the thickness of said sheet ranges from 2.0 mm to 6.0 mm.

3. A sterile flexible bone sheet according to claim 1 wherein the thickness of said cortical layer ranges from 1 mm to 4 mm and the thickness of said cancerous layer ranges from 1 mm to 4 mm.

4. A sterile flexible bone sheet according to claim 1 wherein said sheet has from 1% to 5% hyaluronic acid by weight.

5. A sterile flexible bone sheet according to claim 1 wherein said cortical and said cancellous bone comprises from 99% to 95% by weight of the bone sheet.

6. A sterile flexible bone sheet according to claim 1 wherein said demineralized sheet has residual calcium ranging from 3.0% to 8.0% by weight of the demineralized bone mass.

7. A sterile flexible bone sheet according to claim 1 wherein said demineralized sheet has a neutral pH.

8. A sterile flexible bone sheet according to claim 1 wherein said demineralized bone sheet has an osmolality ranging from 290 mmol/kg to 310 mmol/kg.

9. A sterile flexible bone sheet according to claim 1 wherein said cortical cancellous bone sheet comprises from 99% to 95% by weight of the demineralized bone and from 1% to 5% by weight from a group consisting of hyaluronic acid, sodium hyaluronate and derivations thereof.

10. A sterile flexible bone sheet according to claim 1 wherein said cortical cancellous bone sheet is cut from tibial allograft tissue.

11. A sterile flexible bone sheet according to claim 1 wherein said cortical cancellous bone sheet is cut from femoral allograft tissue.

12. A sterile flexible bone sheet according to claim 1 wherein said cortical cancellous bone sheet is cut from pelvic allograft tissue.

13. A sterile flexible bone sheet according to claim 1 wherein said cortical cancellous bone sheet is cut from cancaneal allograft tissue.

14. A sterile flexible bone sheet for use during the in vivo replacement or reformation of preselected portions of a human bone comprising a continuous unitary sheet of demineralized natural bone including a cortical layer portion which interfaces with a cancellous layer portion with the thickness of said bone sheet ranging from 2.0 mm to 6.0 mm, said sheet having hyaluronic acid or derivatives thereof with a molecular weight over 700,000 Daltons added thereto at a concentration of 1.0 to 4.0 mg/ml, said sheet being flexible for application to a bone to be repaired without damage to the sheet, said sheet being capable of inducing osteogenesis at the bone region.

15. A sterile flexible bone sheet according to claim 14 wherein the thickness of said cortical portion ranges from 1 mm to 3 mm and the thickness of said cancerous portion ranges from 1 mm to 3 mm.

16. A sterile flexible bone sheet according to claim 14 wherein said demineralized sheet has residual calcium ranging from 3.0% to 8.0% by weight of the demineralized bone mass.

17. A sterile flexible bone sheet according to claim 14 wherein said demineralized sheet has a neutral pH.

18. A sterile flexible bone sheet according to claim 14 wherein said demineralized bone sheet has an osmolality ranging from 290 mmol/kg to 310 mmol/kg.

19. A sterile flexible bone sheet according to claim 14 wherein said demineralized bone sheet comprises from 99% to 95% by weight of the demineralized cortical cancellous bone.

20. A sterile flexible bone sheet according to claim 14 wherein said cortical layer interfaces with said cancellous layer through a cortical cancellous section.

21. A sterile flexible bone sheet according to claim 14 wherein said cortical cancerous bone sheet is cut from tibial allograft tissue.

22. A sterile flexible bone sheet according to claim 14 wherein said cortical cancerous bone sheet is cut from femoral allograft tissue.

23. A sterile flexible bone sheet according to claim 14 wherein said cortical cancerous bone sheet is cut from pelvic allograft tissue.

24. A sterile flexible bone sheet according to claim 14 wherein said cortical cancerous bone sheet is cut from cancaneal allograft tissue.

25. A sterile flexible bone sheet according to claim 14 wherein said sheet has a width and length ranging from 1–20 cm.

26. A sterile flexible bone sheet for use during the in vivo replacement or reformation of preselected portions of a human bone comprising a continuous unitary sheet of demineralized natural bone with a cortical layer and a cancerous layer with a cortical/cancellous interface, the thickness of said sheet comprising a cortical layer ranging in thickness from 1 mm to 3 mm and a cancellous layer ranging in thickness from 1 mm to 3 mm, the sheet being capable of being bent from its original shape to conform to the configuration of a bone to be repaired without damage to the sheet, said sheet being capable of inducing osteogenesis at the bone region.

27. A sterile flexible bone sheet according to claim 26 wherein said cortical cancellous bone sheet is cut from tibial allograft tissue.

28. A sterile flexible bone sheet according to claim 26 wherein said cortical cancellous bone sheet is cut from femoral allograft tissue.

29. A sterile flexible bone sheet according to claim 26 wherein said cortical cancellous bone sheet is cut from pelvic allograft tissue.

30. A sterile flexible bone sheet according to claim 26 wherein said cortical cancellous bone sheet is cut from cancaneal allograft tissue.

31. A sterile flexible bone sheet for use during the in vivo replacement or reformation of preselected portions of an animal skeletal system comprising of a continuous unitary sheet of demineralized natural bone with a cortical layer and a cancellous layer with a cortical cancerous interface, said demineralized bone having a residual calcium weight ranging from 3.0% to 8.0% by weight of the demineralized bone mass with the thickness of said sheet ranging from 2.0 mm to 8.0 mm, said sheet containing buffered hyaluronic acid or a derivative of same with a molecular weight over 700,000 Daltons and having a neutral pH, the bone sheet being capable of being bent from its original shape to conform to the configuration of bone to be repaired without damage to the sheet, said sheet being capable of inducing osteogenesis at the bone region.

32. A sterile flexible bone sheet for use during the in vivo replacement or reformation of preselected portions of a human bone comprising a continuous unitary sheet of demineralized natural bone with a cortical layer, a cancerous layer and a cortical cancerous interface said demineralized natural bone having a residual calcium ranging from 3.0% to 8.0% by weight of the demineralized bone mass with the thickness of said sheet ranging from 2.0 mm to 6.0 mm, said sheet containing therein, a hydrogel taken from a group consisting of hyaluronic acid, sodium hyaluronate or derivatives thereof with a molecular weight over 700,000 Daltons and having a neutral pH with an osmolality of 290 mmol/kg to 300 mmol/kg, the sheet being capable of being bent from its original shape to conform to the configuration of a bone to be repaired without damage to the sheet, said sheet being capable of inducing osteogenesis at said bone to be repaired.

33. A method of making a bone sheet with cortical and cancerous portions comprising:
   a). cutting a human bone into substantially tubular portions;
   b). cleaning marrow, blood and lipids from said tubular cut human bone;
   c). cutting said cleaned tubular bone longitudinally along its length;
   d). demineralizing said cut tubular bone rendering the same flexible; and
   e). pulling the ends of said bone formed by said longitudinal cut apart to form a bone sheet with cortical and cancellous portions.

34. A sterile flexible bone sheet according to claim 33 including the step of adding 1% to 5% hyaluronic acid by weight to the bone sheet.

35. A sterile flexible bone sheet according to claim 33 wherein said sheet is demineralized to have residual calcium ranging from 3.0% to 8.0% by weight of the demineralized bone mass.

36. A sterile flexible bone sheet according to claim 33 wherein said demineralized sheet has a neutral pH.

* * * * *

UNITED STATES PATENT AND TRADEMARK OFFICE
CERTIFICATE OF CORRECTION

| | | |
|---|---|---|
| PATENT NO. | : 6,998,135 B1 | |
| APPLICATION NO. | : 09/853761 | |
| DATED | : February 14, 2006 | |
| INVENTOR(S) | : Moon Hae Sunwoo, Arthur A. Gertzman and Bruce Stroever | |

It is certified that error appears in the above-identified patent and that said Letters Patent is hereby corrected as shown below:

Column 3,
Lines 28 and 47, replace "cancerous" with -- cancellous --;

Column 4,
Line 44, replace "cancerous" with -- cancellous --;

Column 5,
Lines 5, 8, 10, 11, 23, 24, and 34, replace "cancerous" with -- cancellous --;

Column 6,
Line 43, before "is trimmed" insert -- bone --;
Line 61, replace "–70c" with -- –70C° --;

Column 7,
Lines 21 and 67, before "is trimmed" insert -- bone --;
Line 39, replace "–70c" with -- –70C° --;

Column 8,
Line 44, before "is trimmed" insert -- bone --;
Line 44, replace "uniforn1" with -- uniform --;
Lines 18 and 61, replace "–70c" with -- –70C° --;

Column 9,
Line 35, replace "cancerous" with -- cancellous --;

Column 10,
Lines 9 and 57, replace "cancerous" with -- cancellous --;

Column 11,
Lines 9, 12, 15, 18, 26, and 51, replace "cancerous" with -- cancellous --;

UNITED STATES PATENT AND TRADEMARK OFFICE
CERTIFICATE OF CORRECTION

PATENT NO. : 6,998,135 B1
APPLICATION NO. : 09/853761
DATED : February 14, 2006
INVENTOR(S) : Moon Hae Sunwoo, Arthur A. Gertzman and Bruce Stroever It is certified that error appears in the above-identified patent and that said Letters Patent is hereby corrected as shown below:

Column 12,
Lines 14, 15, and 28, replace "cancerous" with -- cancellous --;

Signed and Sealed this

Twenty-seventh Day of October, 2009

David J. Kappos
*Director of the United States Patent and Trademark Office*